(12) United States Patent
Tyler

(10) Patent No.: US 9,655,778 B2
(45) Date of Patent: May 23, 2017

(54) POSITION RESPONSIVE FLOW ADJUSTING IMPLANTABLE DEVICE AND METHOD

(71) Applicant: Thomas D. Tyler, San Carlos, CA (US)

(72) Inventor: Thomas D. Tyler, San Carlos, CA (US)

( * ) Notice: Subject to any disclaimer, the term of this patent is extended or adjusted under 35 U.S.C. 154(b) by 179 days.

(21) Appl. No.: 14/797,450

(22) Filed: Jul. 13, 2015

(65) Prior Publication Data
US 2017/0014270 A1    Jan. 19, 2017

(51) Int. Cl.
*A61M 5/00* (2006.01)
*A61F 9/007* (2006.01)

(52) U.S. Cl.
CPC ................. *A61F 9/00781* (2013.01)

(58) Field of Classification Search
CPC ....... A61B 3/16; A61M 27/00; A61M 27/002; A61M 27/006; A61M 27/008; A61F 9/00781; A61F 11/002
USPC ............................................................. 604/9
See application file for complete search history.

(56) References Cited

U.S. PATENT DOCUMENTS

| | | | |
|---|---|---|---|
| 5,300,020 | A | 4/1994 | L'Esperance, Jr. |
| 5,411,473 | A | 5/1995 | Ahmed |
| 6,077,299 | A | 6/2000 | Adelberg et al. |
| 6,168,575 | B1 | 1/2001 | Soltanpour |
| 6,186,974 | B1 | 2/2001 | Allan et al. |
| 6,508,779 | B1 | 1/2003 | Suson |
| 6,589,198 | B1 | 7/2003 | Soltanpour et al. |
| 6,726,664 | B2 | 4/2004 | Yaron et al. |
| 6,827,700 | B2 | 12/2004 | Lynch et al. |
| 8,603,024 | B2 * | 12/2013 | Bohm ................ A61B 3/16 604/9 |
| 8,753,305 | B2 | 6/2014 | Field et al. |
| 8,945,038 | B2 | 2/2015 | Yablonski |
| 8,998,838 | B2 | 4/2015 | Yalamanchili |
| 2014/0024995 | A1 * | 1/2014 | Seaver ............ A61M 27/006 604/10 |

FOREIGN PATENT DOCUMENTS

| | | |
|---|---|---|
| SU | 1738279 A1 | 6/1992 |
| WO | WO 99/66862 A1 | 12/1999 |
| WO | WO 2009/066133 A1 | 5/2009 |

OTHER PUBLICATIONS

Bonomi, L. et al., Vascular risk factors for primary open angle glaucoma: the Egna-Neumarkt Study. Ophthalmology 107(7), 1287-1293 (2000).
Ernest, PJ et al., An evidence-based review of prognostic factors for glaucomatous visual field progression. Ophthalmology 120(3), 512-9 (2013).
Leske, MC et al., Incident open-angle glaucoma and blood pressure. Arch. Ophthalmol. 120(7), 954-959 (2002).

(Continued)

*Primary Examiner* — Philip R Wiest
(74) *Attorney, Agent, or Firm* — Sheppard, Mullin, Richter & Hampton LLP

(57) ABSTRACT

A position sensitive implant is described which comprises a flow channel which is provided with a value which will automatically adjust flow rate through the flow channel depending on whether the flow channel is generally vertical or generally horizontal. The implant may be a shunt used to treat glaucoma.

14 Claims, 2 Drawing Sheets

(56) References Cited

OTHER PUBLICATIONS

Stewart, WC et al., Factors associated with long-term progression or stability in primary open-angle glaucoma. Am. J. Ophthalmol. 130(3), 274-9 (2000).
Tielsch, JM et al., Hypertension, perfusion pressure, and primary open angle glaucoma. A population-based assessment. Arch. Ophthalmol. 113(2), 216-221 (1995).

* cited by examiner

POSITION RESPONSIVE FLOW ADJUSTING IMPLANTABLE DEVICE AND METHOD

BACKGROUND

The present disclosure relates generally to devices that can be implanted in the body, e.g., in the eye, brain or other tissue, to facilitate draining fluids from body locations. The present disclosure more particularly describes embodiments of the present invention which can be used to treat glaucoma.

Glaucoma is a significant public health problem because it is a major cause of blindness. Glaucoma is a form of optic neuropathy, i.e., a disorder of the optic nerve, that is associated with an increase in intra-ocular pressure ("IOP") resulting from the eye lacking the ability to relieve the pressure in the anterior chamber of the eye caused by an abnormal buildup in the anterior chamber of the clear fluid known as "aqueous humor." Aqueous humor, which is formed in the ciliary body in the posterior chamber of the eye, usually at a rate of about 2.5 microliters per minute, enters the anterior chamber through a cleft between the front of the lens and the back of the iris through the pupillary opening in the iris. When the eye is functioning normally, the aqueous humor flows out of the anterior chamber at the same or substantially the same rate as it enters and, as a result, the pressure in the eye remains safely within the normal range of about 12 to 22 mmHg. The major route of outflow of aqueous humor from the anterior chamber is through the trabecular meshwork and into Schlemm's Canal. This route is pressure dependent. When it becomes impeded, the IOP can become elevated because the inflow of aqueous humor is not balanced by outflow until the pressure in the eye rises sufficiently to overcome the impediment to outflow. The result of this increase in pressure is that pressure is transmitted to the vitreous body which, in turn, presses the retina against the choroid which compresses the blood vessels that feed the retina. In time this can result in loss of vision, both peripheral and central, and eventually lead to complete blindness.

One known mode of treatment of elevated IOP has been to implant a shunt which transmits aqueous fluid from the anterior chamber through the trabecular mesh and into Schlemm's Canal and/or other drainage channels which exist in the eye. Shunts which have been previously developed range from the very simple to the substantially complex. It has been found that even after shunts have been implanted to relieve elevated IOP, changes in IOP can occur and attempts to sense such changes in pressure and adjust flow through the shunt have been made. One cause of changes in IOP is body position such that moving from a standing position to a prone or supine position will cause changes in IOP and this, of course, means that IOP can be expected to be different depending upon whether a person is awake and normally active or asleep in a horizontal position. Embodiments of the present invention address the changes in IOP which result from changes in body position, but do not involve pressure sensing. Instead, body position is sensed and flow of aqueous humor is adjusted accordingly.

SUMMARY

The shunts described herein comprise a passage way for the flow of aqueous humor combined with a valve system to adjust this flow in response to changes in body position. In one embodiment, the valve system is arranged such that a flexible membrane bounds one side of the flow passage and a closed container on the other side of the flexible membrane contains a buoyant member which will change location based on body position such that when a person is standing such that IOP is lower, the buoyant member presses against the flexible membrane to reduce the cross section of the flow channel and thereby automatically adjusts to a lower flow rate and when the person is lying down, the buoyant member automatically moves out of contact with the flexible membrane to permit a greater flow rate to accommodate the increase in IOP. In a preferred embodiment the lower flow rate when the person is in the standing position is increased to a higher flow rate when the person is in a horizontal position by removing the restriction to flow. This reduces the impediment to flow caused by the restriction and reduces the elevated IOP which occurs during sleep.

DETAILED DESCRIPTION

The following description is addressed to embodiments of the present invention comprising an aqueous humor shunt device which, in addition to diverting aqueous humor into the eye from the anterior chamber, through the trabecular mesh and into a drainage channel, alters flow volume depending upon body position, i.e., becomes a shunt with an adjustable valve. The shunt of the present invention may be deployed such that it permits drainage into various drainage channels including one or more of Schlemm's Canal, a uveoscleral route or an intrascleral route.

Shunts of various types have been proposed for the treatment of glaucoma. Among these are the shunts described in U.S. Pat. Nos. 8,372,026; 8,771,217 and 8,945,038, the disclosures of each of which are incorporated herein by reference. Those patents disclose shunts which are said to accomplish drainage of aqueous humor, but are not adjustable and thus are not able to respond to changes in intraocular pressure ("IOP"). Some workers have designed systems which respond to change in IOP, e.g., those described in U.S. Pat. Nos. 8,603,024 and 8,753,305, the disclosures of which are incorporated herein by reference, but the systems described in those patents are complex, depend on pressure sensing, and involve the use of multiple valves, sensors, actuators, and other components. Still other patents, e.g., U.S. Pat. Nos. 8,771,220 and 8,998,838, describe shunts which are responsive to changes in IOP using reed valves and needle values. However, none of the devices described in these prior art patents is a shunt designed to respond to changes in body position without sensing pressure.

The shunts described herein are designed to respond to the position of the patient, such as standing, lying down and intermediate positions. They are useful as glaucoma shunts and could be used in other devices such as intra-cranial shunts or other anatomical flow devices that would benefit from position responsive valving.

Figure 1:
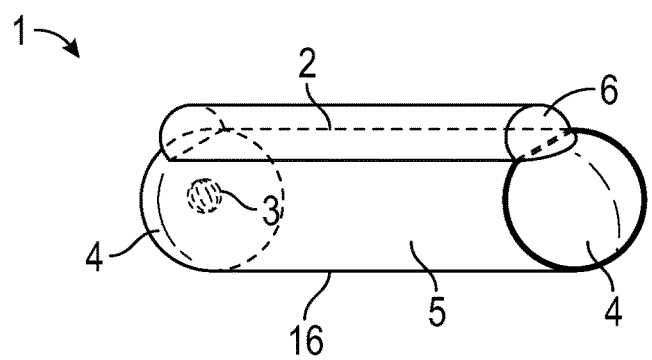
FIG. 1 illustrates an embodiment of the present invention in which the flow passage of the shunt is not restricted.

One embodiment of the present invention is illustrated schematically in FIG. 1. As there shown, the shunt 1 comprises two principal elements, the fluid transport tube 6 which conveys the aqueous humor out of the anterior chamber and chamber 16 which contains a fluid 5 in which buoyant element 3 floats. Chamber 16 is closed by end caps 4. Chamber 16 and fluid transport tube 6 are divided by membrane 2. Buoyant element 3 moves according to the body position of the person in whom it is implanted. IOP is less when a person is standing and increases when a person assumes a supine or prone position such as when sleeping, while blood pressure decreases during sleep while IOP rises. IOP must be maintained within a viable range and when too high or too low, damage to the eye can result. In this regard, it is to be noted that the eye produces fluid at different diurnal rates and filters the fluid out of the eye at variable rates based on body position. The eye is also perfused with blood depending on blood pressure which also varies throughout each day. Eye damage can occur either through the direct effect of IOP on the ocular tissues and/or its effect of limiting ocular perfusion by blood.

Glaucoma is a disease of the eye affecting the optic nerve that can lead to blindness if untreated. It is associated with elevated IOP which is incompatible with optic nerve viability. In addition, since glaucomatous damage can occur and is seen to progress despite low IOP, ocular perfusion should also be considered as a pathological factor. Perfusion of the eye is dependent upon IOP retarding blood perfusion which in turn is relative to mean ocular blood pressure ("MOPP"). In glaucomatous patients, when IOP is greatest MOPP is lowest. The difference between arterial blood pressure and IOP is termed the ocular perfusion pressure (OPP). Sufficient OPP is necessary for ocular organs to received adequate blood supply to maintain a healthy eye. When a person lies down, IOP rises, but, conversely, when a person sleeps, blood pressure decreases. This reduces OPP. Thus, a higher flow rate will reduce a higher IOP during sleep and will help keep OPP at a desirable level.

The shunts of the present invention alter flow volume depending upon body position and provide advantageous additional protection against glaucomatous damage when IOP is elevated while blood pressure is low. When a person is standing such that IOP is lower, the shunt operates as a valve which automatically adjusts to permit sufficient flow to achieve normal IOP, but also restricts flow to provide a pressure relief capability by permitting a higher flow rate when the person with the shunt is in a horizontal position. Thus, when the person is lying down, as when sleeping, the valve adjusts to a greater flow rate to accommodate the increase in IOP, thereby maintaining ocular viability.

Figure 2:
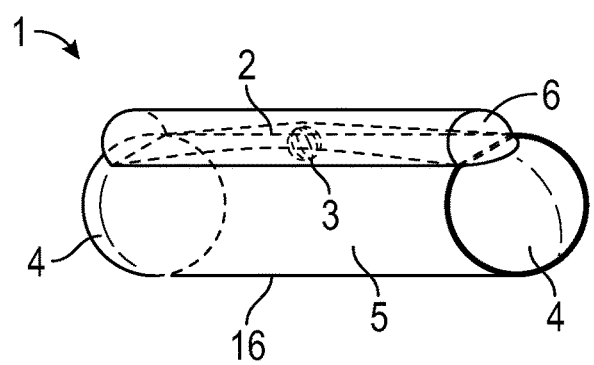
FIG. 2 illustrates an embodiment of the shunt in which the flow channel is restricted.

The shunts of the present invention are installed in the eye such that when a person is in an upright position the drainage device is perpendicular to gravitational direction, i.e., generally horizontal, which causes buoyant element 3 to move adjacent to membrane 2 as shown in FIG. 2 thereby moving membrane 2 from a first position to a second position in which the flow rate through fluid transport tube 6 is less than when the flow channel is unrestricted. When the person is lying down, the shunt 1 will be aligned in the gravitational direction, i.e., generally vertical, and buoyant element 3 will move to an end of chamber 16 away from the diaphragm, thereby returning the shunt to its first configuration shown in FIG. 1 in which fluid transport tube 6 is unrestricted. If the person is in a bending position, the shunt will be at an angle other than perpendicular to the gravitational direction and, depending upon the design of the shunt, the buoyant element may function to restrict fluid flow in tube 6 to a lesser extent than when the person is lying down.

Figure 3:
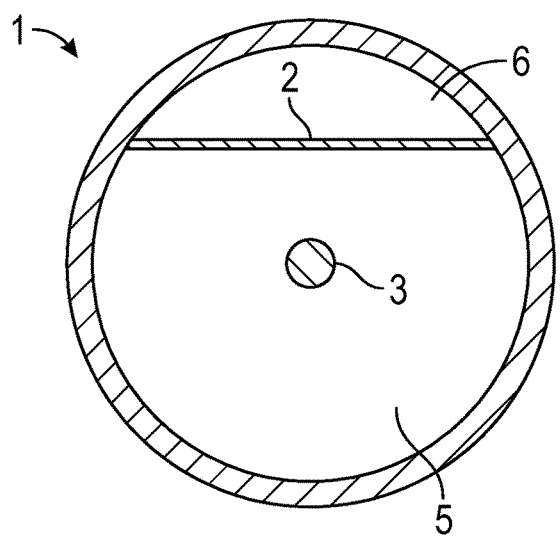
FIG. 3 is a cross sectional view of this embodiment of the invention in which the buoyant member is not in contact with the flexible membrane.
Figure 4:
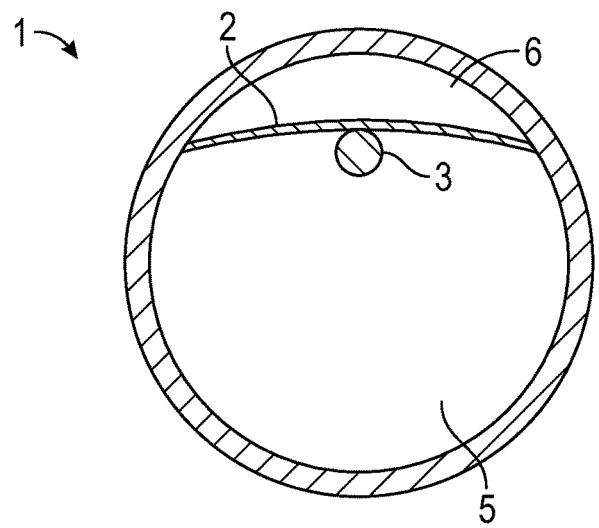
FIG. 4 is a cross sectional view in which the buoyant member is in contact with the flexible membrane such that the flow channel is restricted to some extent.
Figure 5:
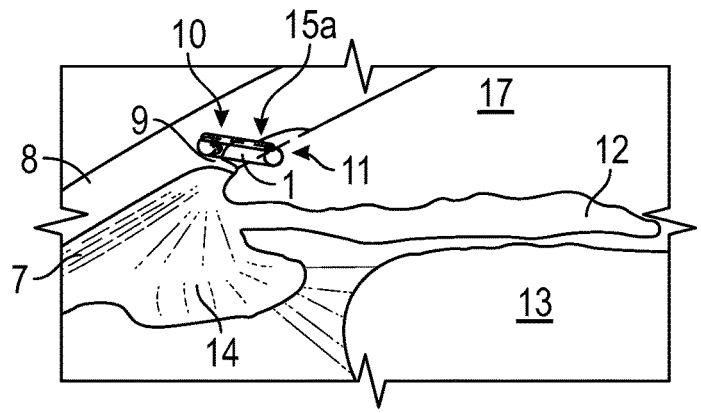
FIGS. 5-6 illustrate the shunt of the present invention implanted in such a manner to direct flow from the anterior chamber to different drainage channels.
Figure 6:
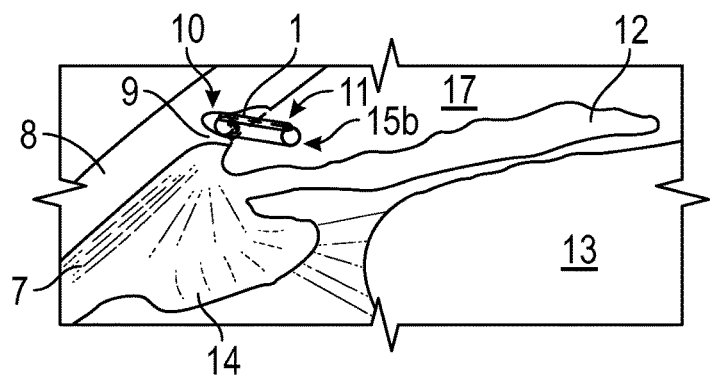

FIG. 3 is a cross-sectional view of the embodiment of FIG. 1 in which buoyant element is out of contact with membrane 2. FIG. 4 is a cross-sectional view of FIG. 2 in which buoyant element 3 is in contact with membrane 2. FIG. 5 shows the device 1 of FIG. 1 implanted in the eye in a manner 15a such that it drains aqueous humor from the anterior chamber 17 into the intrascleral space. The remaining elements of the anatomy of the eye are the posterior ciliary muscle 7, the sclera 8, the scleral spur 9, Schlemm's Canal 10, the trabecular meshwork 11, the iris 12, the lens 13 and the ciliary body 14. FIG. 6 illustrates the device of FIG. 1 implanted in a manner 15b such that it drains into Schlemm's Canal 10. FIG. 7 illustrates device 1 of FIG. 1 implanted 15c such that it drains into a uveoscleral channel.

Chamber 16 may be manufactured from a variety of materials including biocompatible polymers such as silicones, polytetrafluoroethylene, polypropylene or other biocompatible polymers well known to those skilled in the art. Biocompatible metals could also be used including nitinol, stainless steel, and titanium, alone or in combinations with polymers. The diaphragm 2 could be made of the same materials as the chamber 16, but would be thinner and more flexible than chamber 16. Tubular flow channel 6 could be made from any of the foregoing materials and could be fabricated as a single unit or attached to container 16 by well-known techniques such as micro-welding or others known to those skilled in the art. The following dimensions are generally suitable, but not mandatory, for the ocular version of the shunts of the present invention:

length of chamber 16—2 mm to 10 mm, diameter of chamber 16—0.2 mm to 4 mm, length of tubular flow channel 6—1 mm to 10 mm, diameter of lumen of tubular flow channel 6—0.1 mm to 3.5 mm, thickness of flexible diaphragm 2—0.1 mm to 1 mm, length of membrane 2—2 mm to 10 mm, width of membrane 2—0.2 mm to 4 mm.

The shape of chamber 16 and tubular flow channel 6 could be any of a wide variety of shapes including cross-sectional shapes which are rectangular, circular, ovoid, spherical, and could be cylindrical, conical, ellipsoidal, polyhedral or combinations of the above. Buoyant element 3 could be fabricated from any non-soluble biocompatible material with a specific gravity less than the fluid 5 in chamber 16 such that it has sufficient buoyancy to accomplish the intended purpose of the invention. The shape of buoyant element 3 may be virtually any shape which would not interfere with its functional purpose nor damage membrane 2 and buoyant element 3 may be solid or hollow. The number of buoyant devices may range over a broad spectrum, e.g., from 1 to 100, and the size thereof may also have a wide range including nano-particles to 1 micron to 1 mm or more.

The fluid 5 in chambers 16 should be biocompatible and have a specific gravity than that of buoyant element 3. Thus, the choice of fluid 5 will depend, in part, on the choice of material 4 buoyant element 3. Among the fluids which could be used are silicone oil, perfluorinated liquids, semifluorinated alkanes, liquid polymers or any other liquid having the desired biocompatibility and specific gravity.

The configuration of the outer shell of the shunt of the present invention can vary widely and shunts known in the art, such as these disclosed in U.S. Pat. Nos. 8,771,217 and 8,945,038 can be modified by providing them with a position responsive valve such as that shown in FIGS. 1 and 2. Thus, possible configurations include, but are not limited to generally cylindrical shunts, T-shaped shunts, etc. The shunts of the present invention can be configured to connect with more than one drainage channel in the eye.

The foregoing description of specific embodiments is not intended to be limited to those embodiments, but rather the present invention is of the full scope of the appended claims.

The invention claimed is:

1. A position-sensitive implantable device comprising:
   a tubular flow channel member, a closed chamber containing a fluid adjacent to said flow channel,
   a flexible membrane separating said flow channel and said chamber, and
   a position-responsive buoyant element in said chamber which is adapted to be in contact with said membrane when said device is in a generally horizontal position and out of contact with said membrane when said device is in a generally vertical position,
   whereby said buoyant element is adapted to reduce the rate of flow of fluid through said flow channel when the buoyant element is in contact with said membrane.

2. The device of claim 1 wherein said device is an intraocular shunt.

3. The device of claim 2 wherein said shunt is adapted to convey aqueous humor from the anterior chamber of an eye, through the trabecular meshwork of the eye and into at least one drainage channel of the eye.

4. The device of claim 3 wherein said flow channel is adapted to direct flow into Schemm's Canal.

5. The device of claim 3 wherein said flow element is adapted to direct flow into the intrascleral space.

6. The device of claim 3 wherein the flow channel is adapted to direct flow into a uveoscleral channel.

7. The device of claim 1 wherein the specific gravity of the fluid in said chamber is greater than the specific gravity of said buoyant element.

8. A position sensitive implant for treating glaucoma in the eye of a person comprising:
   a tubular flow channel for conveying aqueous humor from the anterior chamber of an eye, through the trabecular meshwork of the eye and into a drainage channel of the eye,
   a closed chamber containing a liquid adjacent to said flow channel,
   a flexible membrane separating said flow channel and said chamber, and
   a position-sensitive buoyant element in said chamber which is adapted to be in contact with said membrane when the person is in an upright position and out of contact with said membrane when the person is lying down,
   whereby the buoyant element is adapted to reduce the flow rate of aqueous humor through the flow channel when the buoyant element is in contact with said membrane.

9. The implant of claim 8 wherein said flow channel is adapted to direct flow into Schlemm's Canal.

10. The implant of claim 8 wherein said flow channel is adapted to direct flow into the subscleral space.

11. The implant of claim 8 wherein the flow channel is adapted to direct flow into a uveoscleral channel.

12. The implant of claim 8 wherein the specific gravity of the liquid in said chamber is greater than the specific gravity of said buoyant element.

13. A method for compensating for changes in internal body pressures comprising implanting a device having a tubular flow channel member, a closed chamber containing a fluid adjacent to said flow channel, a flexible membrane separating said flow channel and said chamber and a position responsive buoyant element in said chamber which is adapted to be in contact with said membrane when said device is in a generally horizontal position and out of contact with said membrane when said device is in a generally vertical position, whereby said buoyant element reduces the rate of flow through said flow channel when said buoyant element is in contact with said membrane.

14. A method for compensating for changes in intraocular pressure caused by changes in body position comprising implanting a device comprising a tubular flow channel for conveying aqueous humor from the anterior chamber of an eye through the trabecular meshwork of the eye and into a drainage channel of the eye, a closed chamber containing a liquid adjacent to said flow channel, a flexible membrane separating said flow channel and said chamber, and a position-sensitive buoyant element in said chamber which is adapted to be in contact with said membrane when the body is in an upright position and out of contact with said membrane when the body is in a horizontal position, whereby said buoyant element reduces the flow rate of aqueous humor through the flow channel when the buoyant element is in contact with the membrane.

* * * * *